United States Patent [19]

Ruge

[11] 4,265,227

[45] May 5, 1981

[54] INFANT EXTREMITY POSITIONER AND ILLUMINATOR

[75] Inventor: Walter Ruge, Tampa, Fla.

[73] Assignee: The Hospital and Welfare Board of Hillsborough County, Fla.

[21] Appl. No.: 81,580

[22] Filed: Oct. 3, 1979

[51] Int. Cl.³ .............................................. A61B 1/06
[52] U.S. Cl. .................................... 128/23; 350/238; 269/322; 269/328
[58] Field of Search .................... 128/21, 22, 23, 362, 128/395, 396, 397, 398, 663, 666, 665, 667; 269/322, 328; 350/87, 90, 235, 238; 362/804; 240/11

[56] References Cited

U.S. PATENT DOCUMENTS

| | | |
|---|---|---|
| 711,550 | 10/1902 | Zibulski . |
| 1,015,730 | 1/1912 | Gill ........................................ 350/238 |
| 1,887,022 | 11/1932 | Hoffman et al. . |
| 2,266,230 | 12/1941 | Mazzeo et al. ...................... 128/327 |
| 2,551,617 | 5/1951 | Maybert ............................... 128/214 |
| 2,700,381 | 1/1955 | Powell ................................... 128/1 |
| 2,790,438 | 4/1957 | Taplin et al. ......................... 128/633 |
| 3,215,834 | 11/1965 | Tayman ................................ 250/54 |
| 3,323,150 | 6/1967 | Rehder ................................. 5/336 |
| 3,358,141 | 12/1967 | Hoffman et al. ..................... 250/50 |
| 3,463,142 | 8/1969 | Harte .................................... 128/633 |
| 3,521,625 | 7/1970 | Mackey ................................ 128/133 |
| 3,526,222 | 9/1970 | Dreibelbis ............................ 128/134 |
| 3,606,885 | 9/1971 | Lund .................................... 128/134 |
| 3,628,525 | 12/1971 | Polanyi et al. ...................... 128/633 |
| 3,650,523 | 3/1972 | Darby, Jr. ............................ 269/328 |
| 3,729,752 | 5/1973 | Huggins ............................... 5/93 R |
| 3,779,540 | 12/1973 | Boudrew .............................. 269/322 |
| 3,892,399 | 7/1975 | Cabansag ............................. 269/328 |
| 3,897,777 | 8/1975 | Morrison .............................. 269/322 |
| 4,045,678 | 8/1977 | Rickard ................................ 250/451 |
| 4,067,565 | 1/1978 | Daniels ................................ 269/328 |
| 4,078,560 | 3/1978 | Hill ....................................... 128/133 |

FOREIGN PATENT DOCUMENTS 616556 7/1935 Fed. Rep. of Germany .......... 128/396

Primary Examiner—Robert W. Michell
Assistant Examiner—J. L. Kruter
Attorney, Agent, or Firm—Mason, Fenwick & Lawrence

[57] ABSTRACT

An illuminator for providing high intensity light to an extremity such as an arm or leg of an infant has first and second spaced support blocks on which the extremity is positioned and strap means for holding the extremity in position; a hollow light directing housing is positioned between the support blocks and has an internal mirror reflector which receives light from a remote projector bulb via a fiberglass conduit extending between the projector bulb and the housing with the light being reflected upwardly through an aperture in the upper portion of the housing in which the portion of the extremity to be illuminated is positioned. The aperture in the housing is adjustable to accommodate extremities of various widths.

9 Claims, 5 Drawing Figures

INFANT EXTREMITY POSITIONER AND ILLUMINATOR

BACKGROUND OF THE INVENTION

This invention is in the field of medical equipment and is more particularly directed to means for holding and restraining an extremity of an infant while illuminating a portion thereof for permitting medical procedures such as the insertion of cannulae in blood vessels for performing various medical procedures. Even more particularly, the present invention is directed to means for supporting and illuminating the extremity of an infant without any danger of burning or other injury to the infant.

Numerous medical procedures require the insertion of hypodermic needles or other cannulae in the blood vessels of small infants with such procedures normally being effected in the extremities. Previously, such procedures have been quite difficult in that it is necessary to restrain the extremity against movement and to also illuminate the area in which the procedure is to be effected so as to permit visualization of the blood vessels beneath the skin. Consequently, it is extremely difficult for a single person to perform these procedures and injury of the infant sometimes occurs. While other restraining devices such as U.S. Pat. Nos. 711,550; 1,887,022; 2,266,230; 2,266,231; 2,551,617; 2,700,381; 3,215,834; 3,323,150; 3,358,141; 3,521,625; 3,526,222; 3,606,885; 3,650,523; 3,729,752; 3,892,399; 3,933,154; 4,045,678; 4,067,565 and 4,078,560 have been known, such devices have not proven fully satisfactory in providing safe and secure restraint of the extremity in conjunction with skin illumination with no burn hazard possibility.

Therefore, it is the primary object of this invention to provide means for safely positioning and restraining the extremity of an infant and for also illuminating a portion of the extremity to permit the insertion of cannulae for various medical procedures.

A further object of the present invention is the provision of a new and improved infant extremity positioning, restraining and illuminating means in which there is no danger of burn injury to the infant.

Achievement of the foregoing objects is enabled by the preferred embodiment of the invention which comprises a plastic base plate on which two upwardly extending support blocks are provided. The support blocks are separated from each other and the space between the support blocks receives a light directing housing connected by a flexible fiberglass tube to a light source positioned a distance away from the housing. Light from the fiberglass tube is directed to a mirror in the housing which then directs it upwardly through an opening in the upper portion of the housing in which the infant's extremity is positioned and held by strap means attached to each of the respective block members. The block members include cushion pads on their upper surface on which the extremity is positioned. Since the source of light is not adjacent the infant's skin, but is spaced a substantial distance therefrom, there is no danger of burn injury. Additionally, the aperture in the upper portion of the light directing housing is adjustable in width to accommodate extremities of varying sizes.

DESCRIPTION OF THE PREFERRED EMBODIMENT

Figure 1:
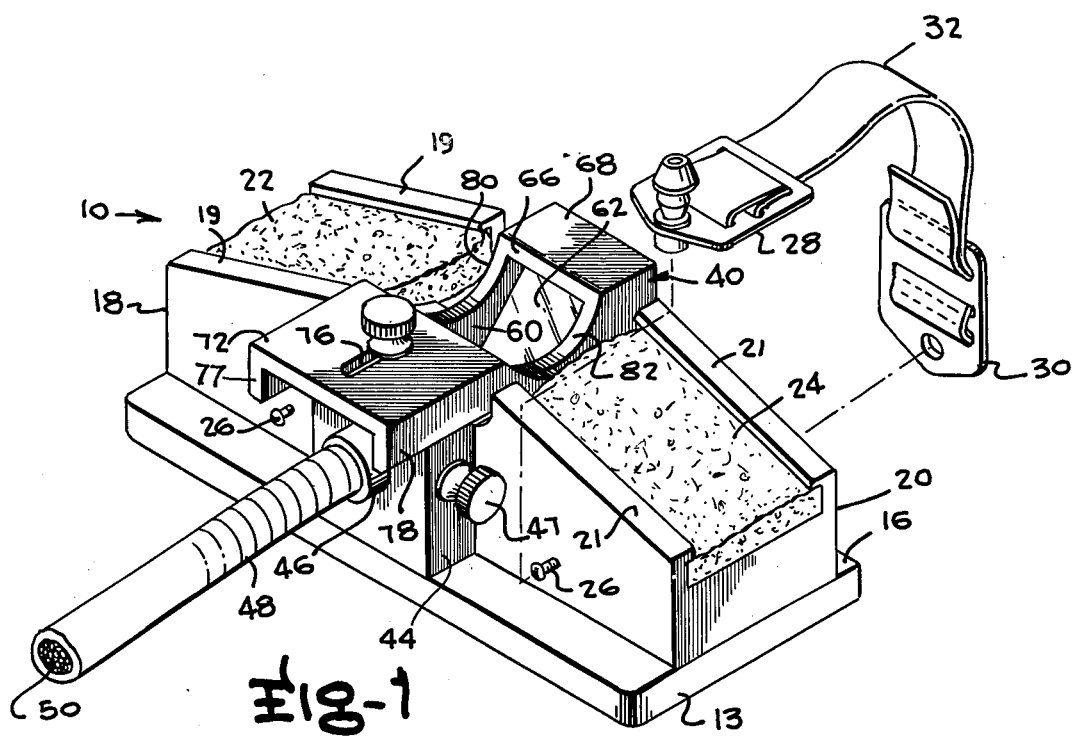
FIG. 1 is a perspective view of the preferred embodiment.
Figure 2:
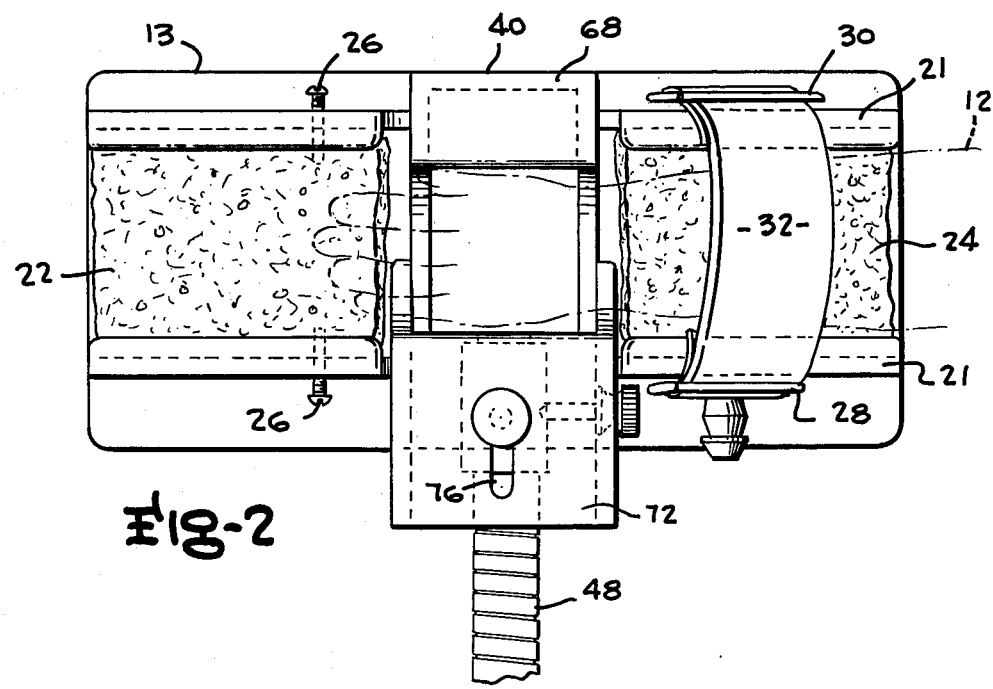
FIG. 2 is a top plan view of the preferred embodiment.

Attention is initially invited to FIG. 1 of the drawings which illustrates the preferred embodiment of the invention, generally designated 10, and which comprises means for restraining and holding an extremity 12 such as the arm and hand of an infant patient as shown in FIG. 2.

More specifically, the preferred embodiment comprises a support base formed of a base plate 13 having a planar lower surface 14 and a planar upper surface 16. Base plate 13 is formed of plastic or other suitable material and provides support for a first support block 18 and a second support block 20 which is identical to block 18. Support blocks 18 and 20 are spaced from each other on the upper planar surface 16 to which they are bonded by adhesive or other suitable means. Each of the support blocks 18 and 20 is provided with an upper surface on which cushion members 22 and 24 are respectively supported and held in position by side flanges 19 of support block 18 and side angle flanges 21 on support block 20. Suitable screws 26 or other connectors are provided on the support blocks for receiving metal buckle plates 28 and 30 provided on opposite ends of rubber, plastic or the like restraining straps 32 of conventional design.

Figure 4:
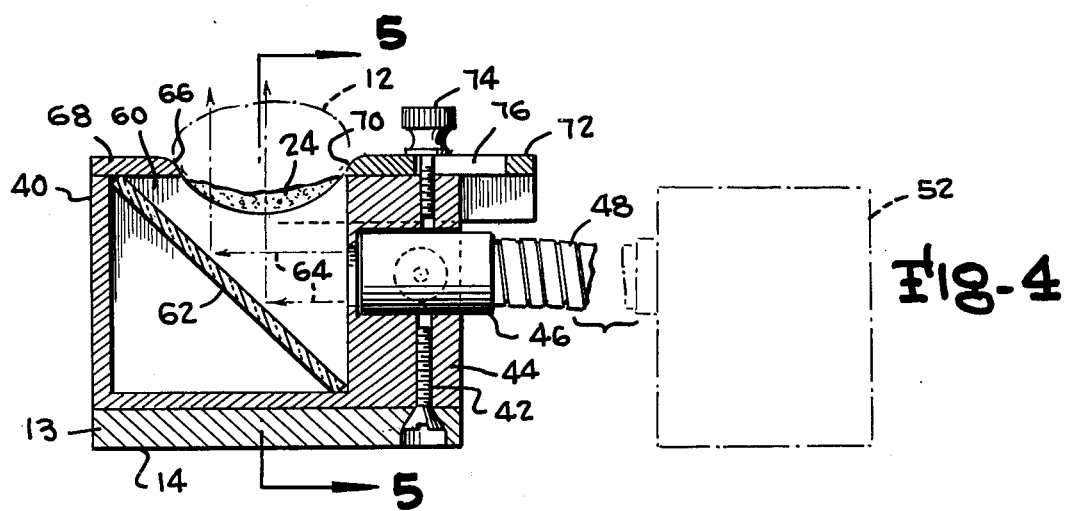
FIG. 4 is a sectional view taken along lines 4—4 of FIG. 3.

A light directing housing 40 is supported on the upper surface 16 of the base plate 13 in the space between the first and second support blocks 18 and 20 with the housing 40 being held on the base plate 13 by screw means 42 as shown in FIG. 4. Housing 40 includes a relatively thick side wall 44 (see FIG. 4) in which a transverse bore is provided for receiving a coupling sleeve 46 mounted on the end of a conventional flexible fiberglass light conductor 50 which is shielded within a spiral stainless steel shield 48 enclosing and surrounding the fiberglass light conductor conduit means 50 as shown in FIG. 1. Coupling sleeve 46 is held in position by clamp screw 47. The end of the fiberglass light conductor 50 opposite the end connected to the tubular fitting 46 is connected to a light source housing 52 in which a projector type bulb is provided for directing concentrated light into the fiberglass light conduit 50. The light source can be of the type such as a Medical General Transilluminator.

Light directing housing 40 includes a hollow interior chamber 60 in which a mirror 62 is mounted for receiving the light rays 64 emanating from the fiberglass light conduit 50 for reflecting the light rays upwardly through an opening provided in the top of the housing onto the extremity 12 positioned in the opening.

The opening in the top of the housing is defined along one side by a rounded edge 66 of a fixed top plate 68 of the housing with the opposite side being defined by a rounded edge 70 of an adjustable movable top plate 72 which is held in adjusted position by a set screw 74 extending through a slot 76 in the adjustable top plate and threadably received within a threaded bore in the relatively thick wall 44. Side flanges 77 and 78 extend downwardly and forwardly of the adjustable top plate 72 and cooperate with downwardly curved upper surfaces of side walls 80 and 82 to define a downwardly extending recess in the housing for receiving the extremity 12 of the infant patient. By adjusting the position of the adjustable top plate 72, etc., the width of the extremity receiving depressed opening can be varied to accommodate extremities of varying widths.

Figure 3:
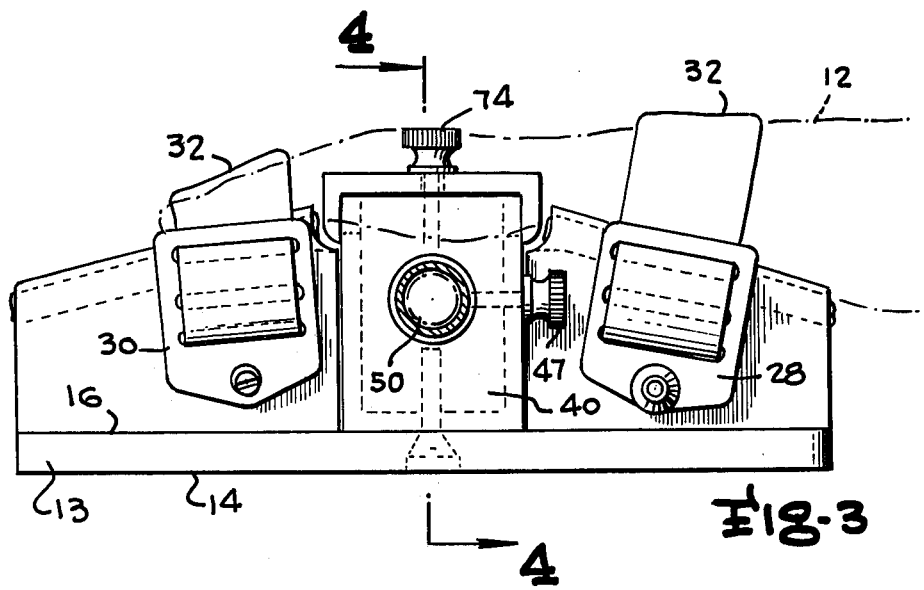
FIG. 3 is a side elevation view of the preferred embodiment.
Figure 5:
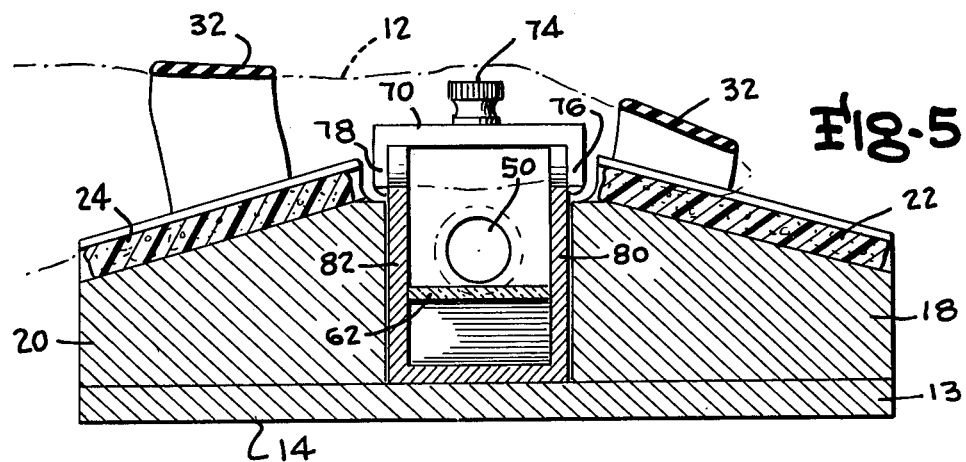
FIG. 5 is a sectional view taken along lines 5—5 of FIG. 4.

The light housing 40 as well as the base plate 13 and blocks 18 and 20 are preferably formed of plastic or the like; however, other materials could be used if desired. By positioning the light source 52 a substantial distance away from the extremity 12 to be illuminated, the danger of injury to the patient by turning is eliminated. When the patient's arm is positioned in the manner shown in FIG. 3 or in FIG. 5, the restraining straps 32 hold the arm in position with the light being directed against the mirror 62 and reflected upwardly to illuminate the skin of the extremity 12 so as to permit the blood vessels to be easily seen to enable medical procedures such as the placement of intravenous or intra arterial cannulae as required for various medical procedures. It should be understood that the scope of the invention is not limited to the preferred embodiment and numerous modifications of same will undoubtedly occur to those of skill in the art. Therefore, the spirit and scope of the invention is to be limited solely by the appended claims.

I claim:

1. A medical device for holding in a restrained manner a human body extremity of a rounded cross-section of varying sizes and having first and second opposed surfaces and for directing illuminating radiation through the first surface of the extremity to transilluminate body tissue therein to permit medical procedures to be effected upon the exposed second surface, said medical device having an axis, said medical device comprising:
    (a) a light directing housing including means for defining an aperture, said aperture in part defined by first and second curved edge surfaces, and means for adjustably disposing said first edge surface with respect to said second edge surface along a direction traverse to said axis in a manner to partially and matingly receive the extremity against said aperture whereby high intensity illumination is directed through the first surface of the extremity;
    (b) means disposed adjacent said aperture for receiving and holding the extremity in a restrained fashion to disposed the first surface thereof in communication with said aperture in a manner to permit unobstructed observation of the second surface;
    (c) light source positioned remotely of said light directing housing; and
    (d) a light conduit extending between said light source and said light directing housing for directing light from said light source through said aperture to transilluminate the body tissue within the extremity restrained in communication with said aperture by said receiving and holding means whereby substantially no heat generated by said light source is transmitted by said light directing housing to the extremity.

2. The invention of claim 1 wherein said receiving and holding means includes a base member, first and second support blocks mounted in space relation on said base member and each having an upper surface and flexible restrainer straps attached to said support blocks and extending over said upper extremity supporting surfaces and wherein said light directing housing is positioned between said support blocks.

3. The invention of claim 1 wherein said receiving and holding means includes a base member, first and second support blocks mounted in spaced relation on said base member and each having an upper surface and flexible restrainer straps attached to said support blocks extendable up over said upper extremity supporting surfaces and wherein said light directing housing is positioned between said first and second support blocks and said upper surfaces of each of said first and second support blocks is canted downwardly and outwardly from said light directing housing.

4. The invention as claimed in claim 3, wherein said aperture defining means comprises a fixed top plate and an adjustable top plate adjustably disposed from said fixed top plate along a direction traverse to said axis; said fixed top plate having a first rounded edge, said first curved edge surface and a third curved edge surface spaced from said first curved edge surface; said adjustable top plate having a second rounded edge, and first and second downwardly extending flanges along opposite sides of said adjustable top plate, said downwardly extending first and second flanges bearing, respectively, said second curved edge surface and a fourth edge surface cooperating respectively, with said first and third edge surfaces to define two variable length sides of said aperture.

5. The invention as claimed in claim 4, wherein said adjustable top plate includes a slot, and said light directing housing includes a screw disposed therein and extending through said slot for permitting said adjustable top plate to be adjustably disposed toward or away from said fixed top plate and holding said adjustable top plate in an adjusted position.

6. The invention of claim 15 wherein there is included cushion pad means mounted on said upper surfaces of said first and second support blocks.

7. An illuminator for providing high intensity light to an extremity of an infant comprising support and restraining means for receiving and restraining against movement an extremity to be illuminated, said support and restraining means including a base member, first and second support blocks mounted in spaced relation on said base member and each having an upper surface, flexible restrainer straps attached to said support blocks and extending over said upper extremity supporting surfaces; a light directing housing including means defining an extremity receiving and positioning aperture in the upper portion of said light directing housing dimensioned to partially receive the portion of the extremity to be illuminated, said light directing housing being positioned between said support blocks and said extremity receiving and positioning aperture in said light directing housing is of adjustable width and is defined on two sides by first and second downwardly curved upper surfaces on two opposed side walls of said light directing housing, a curved edge on a fixed top plate, a curved edge on an adjustable top plate spaced from said fixed top plate and first and second downwardly extending flanges along opposite sides of the adjustable top plate, said downwardly extending flanges having forwardly and downwardly extending protrusions extending alongside said two opposed side walls to cooperate with said downwardly curved upper surfaces thereof to define two variable length sides of said downwardly extending extremity receiving and positioning aperture; a light source positioned externally of said light directing housing; a light conduit extending between said light source and said light directing housing; for reflector means in said light directing housing for directing light from the light conduit upwardly through said extremity positioning and receiving aperture to illuminate an extremity when positioned therein.

8. An illuminator for providing high intensity light to an extremity of an infant comprising support and restraining means for receiving and restraining against movement an extremity to be illuminated, said support and restraining means including a base member, first and second support blocks mounted in spaced relation on said base member and each having an upper surface, cushion pad means mounted on said upper surfaces of said first and second support blocks, flexible restrainer straps attached to said support blocks and extending over said upper extremity supporting surfaces; a light directing housing positioned adjacent said support and restraining means and including means defining an extremity receiving and positioning aperture in the upper portion of said light directing housing dimensioned to partially receive the portion of the extremity to be illuminated, said light directing housing being positioned between said support blocks, said extremity receiving and positioning aperture in said light directing housing being of adjustable width and being defined on two sides by first and second downwardly curved upper surfaces on two opposed side walls of said light directing housing, by a curved edge on a fixed top plate, by a curved edge on an adjustable top plate spaced from said fixed top plate, and by first and second downwardly extending flanges along opposite sides of said adjustable top plate, said downwardly extending flanges having forwardly and downwardly extending protrusions extending alongside said two opposed side walls to cooperate with said downwardly curved upper surfaces thereof to define two variable length sides of said downwardly extending extremity receiving and positioning aperture; a light source positioned externally of said light directing housing; a light conduit extending between said light source and said light directing housing; and reflector means in said light directing housing for directing light from said light conduit upwardly through said extremity receiving and positioning aperture to illuminate the extremity when positioned therein.

9. An illuminator for providing high intensity light to an extremity of an infant comprising support and restraining means for receiving and restraining against movement an extremity to be illuminated, said support and restraining means including a base member, first and second support blocks mounted in spaced relation on said base member and each having an upper surface and flexible restrainer straps attached to said support blocks extendable up over said upper extremity supporting surfaces, cushion pad means mounted on said upper surfaces of said first and second support blocks; a light directing housing including means defining an extremity receiving and positioning aperture in the upper portion of said light directing housing dimensioned to partially receive the portion of the extremity to be illuminated, said light directing housing being positioned between said support blocks and said upper surfaces of said support blocks being canted downwardly and outwardly from said light directing housing, said extremity receiving and positioning aperture in said light directing housing being of adjustable width and being defined on two sides by first and second downwardly curved upper surfaces on two opposed side walls of said light directing housing, by a curved edge on a fixed top plate, by a curved edge on an adjustable top plate spaced from said fixed top plate, and by first and second downwardly extending flanges along opposite sides of said adjustable top plate, said downwardly extending flanges having forwardly and downwardly extending protrusions extending alongside said two opposed side walls to cooperate with the downwardly curved upper surfaces thereof to define two additional sides of said downwardly extending extremity receiving and positioning aperture, said adjustable top plate includes a slot; a set screw in said slot for permitting said adjustable top plate to be positioned in an adjusted position toward or away from said fixed top plate; a light source positioned externally of said light directing housing; a light conduit extending between said light source and said light directing housing; and reflector means in said light directing housing for directing light from said light conduit upwardly through said extremity positioning and receiving aperture to illuminate an extremity when positioned thereon.

* * * * *